US00PP26224P2

(12) United States Plant Patent
Mak

(10) Patent No.: US PP26,224 P2
(45) Date of Patent: Dec. 15, 2015

(54) LILY PLANT NAMED 'TINY NUGGET'

(50) Latin Name: *Lilium hybrida*
Varietal Denomination: Tiny Nugget

(71) Applicant: Niels Johannes Cornelis Mak, Wieringerwerf (NL)

(72) Inventor: Niels Johannes Cornelis Mak, Wieringerwerf (NL)

(73) Assignee: MAK 't ZAND B.V., 't Zand (NL)

( * ) Notice: Subject to any disclaimer, the term of this patent is extended or adjusted under 35 U.S.C. 154(b) by 137 days.

(21) Appl. No.: 13/998,711

(22) Filed: Nov. 26, 2013

(51) Int. Cl.
*A01H 5/02* (2006.01)

(52) U.S. Cl.
USPC ..... Plt./314

(58) Field of Classification Search
USPC ..... Plt./314
See application file for complete search history.

*Primary Examiner* — Keith Robinson
(74) *Attorney, Agent, or Firm* — C. A. Whealy

(57) ABSTRACT

A new and distinct cultivar of Lily plant named 'Tiny Nugget', characterized by its compact and upright plant habit; vigorous growth habit; early and freely flowering habit; upright flower buds; yellow orange-colored flowers with numerous greyed red-colored spots; and good postproduction longevity.

1 Drawing Sheet

Botanical designation: *Lilium hybrida.*
Cultivar denomination: 'TINY NUGGET'.

BACKGROUND OF THE INVENTION

The present Invention relates to a new and distinct cultivar of Lily plant, commercially known as Asiatic Hybrid Lily, botanically known as *Lilium hybrida* and hereinafter referred to by the name 'Tiny Nugget'.

The new Asiatic Hybrid Lily plant is a product of a planned breeding program conducted by the Inventor in 't Zand, The Netherlands. The objective of the breeding program is to develop new compact potted Asiatic Hybrid Lily plants with large attractive flowers and good postproduction longevity.

The new Asiatic Hybrid Lily plant originated from a cross-pollination in 2003 of two unnamed proprietary seedling selections of *Lilium hybrida,* not patented. The new Asiatic Hybrid Lily plant was discovered and selected by the Inventor as a single flowering plant from within the resultant progeny of the stated cross-pollination in a controlled greenhouse environment in 't Zand, The Netherlands in 2006.

Asexual reproduction of the new Asiatic Hybrid Lily plant by bulb scales in a controlled greenhouse environment in 't Zand, The Netherlands since 2008 has shown that the unique features of this new Asiatic Hybrid Lily plant are stable and reproduced true to type in successive generations.

SUMMARY OF THE INVENTION

Plants of the new Asiatic Hybrid Lily have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Tiny Nugget'. These characteristics in combination distinguish 'Tiny Nugget' as a new and distinct Asiatic Hybrid Lily plant:

1. Compact and upright plant habit.
2. Vigorous growth habit.
3. Early and freely flowering habit.
4. Upright flower buds.
5. Yellow orange-colored flowers with numerous greyed red-colored spots.
6. Good postproduction longevity.

Plants of the new Asiatic Hybrid Lily differ primarily from plants of the female parent selection in the following characteristics:

1. Plants of the new Asiatic Hybrid Lily are taller than plants of the female parent selection.
2. Plants of the new Asiatic Hybrid Lily and the female parent selection differ in flower color as plants of the female parent selection have yellow-colored flowers with few spots.

Plants of the new Asiatic Hybrid Lily differ primarily from plants of the male parent selection in the following characteristics:

1. Plants of the new Asiatic Hybrid Lily are more compact than plants of the male parent selection.
2. Plants of the new Asiatic Hybrid Lily have shorter leaves than plants of the male parent selection.
3. Plants of the new Asiatic Hybrid Lily flower later than plants of the male parent selection.

Plants of the new Asiatic Hybrid Lily can be compared to plants of the Asiatic Hybrid Lily 'Tiny Sensation', disclosed in U.S. Plant Pat. No. 17,617. Plants of the new Asiatic Hybrid Lily differ from plants of 'Tiny Sensation' in the following characteristics:

1. Plants of the new Asiatic Hybrid Lily are taller than plants of 'Tiny Sensation'.
2. Plants of the new Asiatic Hybrid Lily have shorter leaves than plants of 'Tiny Sensation'.
3. Plants of the new Asiatic Hybrid Lily flower later than plants of 'Tiny Sensation'.
4. Flowers of plants of the new Asiatic Hybrid Lily have larger and more rounded tepals than flowers of plants of 'Tiny Sensation'.

5. Plants of the new Asiatic Hybrid Lily and 'Tiny Sensation' differ in flower color as plants of 'Tiny Sensation' have yellow and dark red bi-colored flowers.

DESCRIPTION OF THE PHOTOGRAPH

The accompanying colored photograph illustrates the overall appearance of the new Asiatic Hybrid Lily plant showing the colors as true as it is reasonably possible to obtain in colored reproductions of this type. Colors in the photograph may differ slightly from the color values cited in the detailed botanical description which accurately describe the colors of the new Asiatic Hybrid Lily plant.

The photograph comprises a side perspective view of a typical flowering plant of 'Tiny Nugget' grown in a container.

DETAILED BOTANICAL DESCRIPTION

The aforementioned photograph and following observations and measurements describe plants grown during the spring in 15-cm containers in a glass-covered greenhouse in 't Zand, The Netherlands and under cultural practices typically used in Asiatic Hybrid Lily commercial production. During the production of the plants, day temperatures averaged 18° C., night temperatures averaged 15° C. and light levels averaged 6,000 lux. Measurements and numerical values represent averages for typical flowering plants. Plants were 60 days old when the photograph and description were taken. In the following description, color references are made to The Royal Horticultural Society Colour Chart, 2007 Edition, except where general terms of ordinary dictionary significance are used.

Botanical classification: *Lilium hybrida* 'Tiny Nugget'.

Parentage:

*Female, or seed, parent*.—Unnamed proprietary seedling selection of *Lilium hybrida,* not patented.

*Male, or pollen, parent*.—Unnamed proprietary seedling selection of *Lilium hybrida,* not patented.

Plant description:

*Plant and growth habit*.—Upright plant habit; single erect flowering stem with a terminal cluster of flowers; compact and dense plant habit; vigorous growth habit.

*Plant height, soil level to top of flowers*.—About 45 cm.

*Plant diameter or spread*.—About 18 cm.

*Plant circumference*.—About 56 cm.

*Bulbs*.—Diameter: About 10 cm to 20 cm. Texture: Smooth. Color: Close to 155D.

*Flowering stems*.—Diameter: About 7.5 mm. Internode length: About 1.5 cm to 2.5 cm. Strength: Strong. Texture: Smooth, glabrous. Color: Close to 138A.

*Leaves*.—Arrangement: Alternate, simple; sessile; about 86 leaves develop per plant. Length, upper leaves: About 9 cm. Width, upper leaves: About 2 cm. Length, lower leaves: About 10 cm. Width, lower leaves: About 2 cm. Shape: Lanceolate. Apex: Acute. Base: Acutely cuneate. Margin: Entire. Texture, upper and lower surfaces: Glabrous, smooth; leathery. Venation pattern: Parallel. Color: Developing and fully expanded leaves, upper surface: Close to 139A; venation, close to 139A. Developing and fully expanded leaves, lower surface: Close to 137B; venation, close to 137B.

Flower description:

*Flower shape and aspect*.—Flowers umbellate and funnel-shaped; when fully opened, flowers flatten and tepals recurve towards the apex; flower buds face upright and flowers face upright to outwardly.

*Flowering habit*.—Freely flowering habit, large bulbs will produce about seven to ten flowers per flowering stem.

*Fragrance*.—Slightly fragrant; sweet, pleasant.

*Natural flowering season*.—Plants flower in June and July in The Netherlands; early flowering habit, plants can be flowered year-round in the greenhouse and forced to bloom about 60 days after planting bulbs.

*Postproduction longevity*.—Good postproduction longevity, flowers last about 13 days on the plant; tepals not persistent; gynoecium persistent.

*Flower buds*.—Length: About 9.5 cm. Diameter: About 3 cm. Circumference: About 8 cm. Shape: Lanceolate. Color: Close to 154B and 9B; sutures, close to 154B and 9B.

*Flower size*.—Diameter: About 18 cm. Length (height): About 6 cm.

*Perianth*.—Quantity and arrangement: Six tepals per flower arranged in two whorls; tepals imbricate. Tepal length, inner tepals: About 9.5 cm. Tepal width, inner tepals: About 5.5 cm. Tepal length, outer tepals: About 10 cm. Tepal width, outer tepals: About 4 cm. Tepal shape: Lanceolate. Tepal apex: Acute. Tepal margin: Entire. Tepal texture, upper and lower surfaces: Smooth, glabrous. Tepal color: When opening and fully opened, upper surface: Close to 14B; numerous spots, close to 182A; color becoming closer to 162A with development. When opening and fully opened, lower surface: Close to 10B.

*Pedicels*.—Length: About 3.5 cm. Diameter: About 5 mm. Angle: About 45° to 70° from flowering stem. Strength: Strong. Texture: Smooth, glabrous. Color: Close to 138A.

*Reproductive organs*.—Stamens: Quantity per flower: Six. Filament length: About 6.5 cm. Filament color: Close to 4C. Anther length: About 2 cm. Anther color: Close to 164B. Pollen color: Close to 168B. Pistils: Quantity per flower: One. Style length: About 5.5 cm. Style color: Close to 4C. Stigma diameter: About 3 mm. Stigma shape: Lobed. Stigma color: Close to 186A.

*Fruits*.—Length: About 1.7 cm. Diameter: About 4 mm. Color: Close to 144D.

*Seeds*.—No viable seeds have been observed on plants of the new Asiatic Hybrid Lily.

Disease & pest resistance: Resistance to pathogens and pests common to Asiatic Hybrid Lilies has not been observed on plants of the new Asiatic Hybrid Lily.

Garden performance: Plants of the new Asiatic Hybrid Lily have exhibited good tolerance to rain and wind and have been observed to tolerate temperatures from about −2° C. to about 40° C.

It is claimed:

1. A new and distinct Lily plant named 'Tiny Nugget' as illustrated and described.

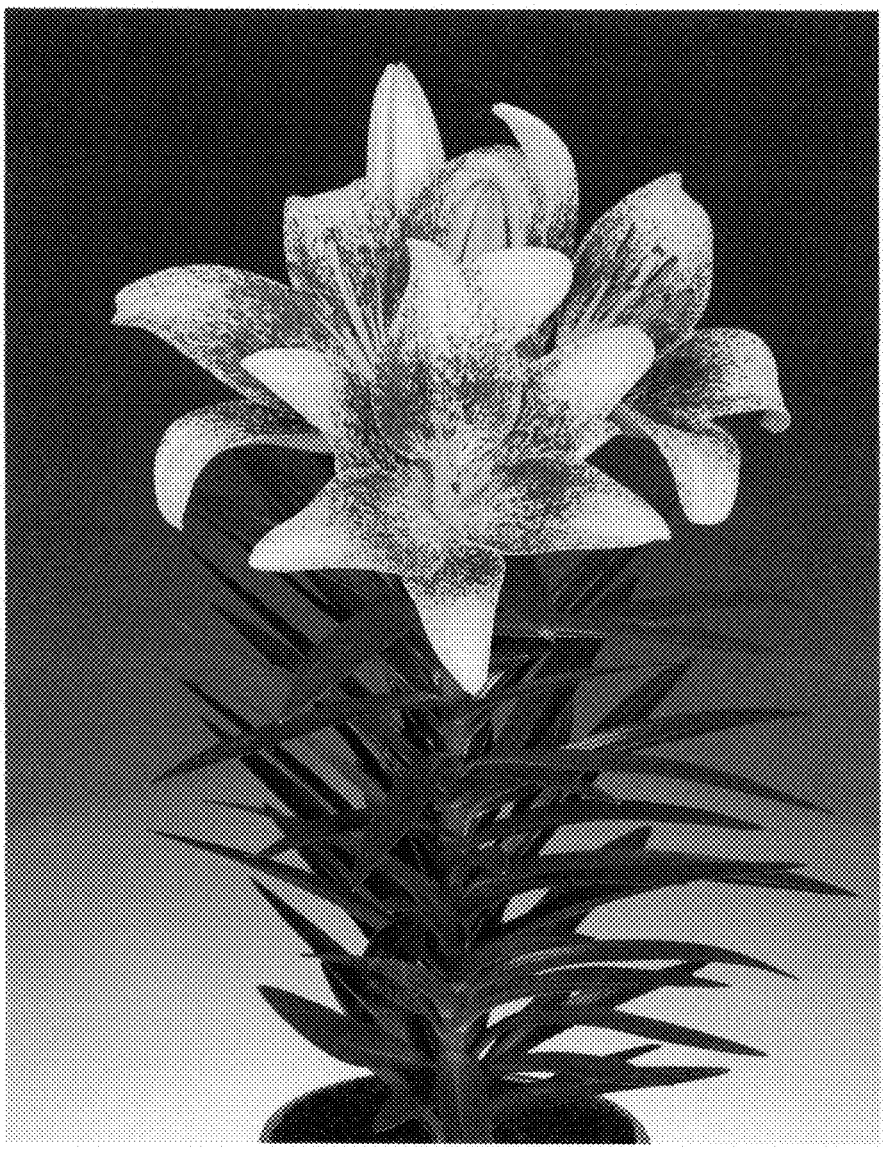

* * * * *